(12) United States Patent
Nilsen et al.

(10) Patent No.: US 6,541,204 B2
(45) Date of Patent: Apr. 1, 2003

(54) METHOD OF REMOVING NUCLEIC ACID CONTAMINATION IN AMPLIFICATION REACTIONS

(75) Inventors: Inge Waller Nilsen, Kvaløysletta (NO); Erling Sandsdalen, Kvaløysletta (NO); Even Stenberg, Kvaløysletta (NO)

(73) Assignee: Norwegian Institute of Fisheries & Aquaculture Ltd. (NO)

(*) Notice: Subject to any disclaimer, the term of this patent is extended or adjusted under 35 U.S.C. 154(b) by 0 days.

(21) Appl. No.: 09/485,110

(22) PCT Filed: Aug. 6, 1998

(86) PCT No.: PCT/GB98/02369

§ 371 (c)(1),
(2), (4) Date: Apr. 10, 2000

(87) PCT Pub. No.: WO99/07887

PCT Pub. Date: Feb. 18, 1999

(65) Prior Publication Data

US 2002/0042052 A1 Apr. 11, 2002

(30) Foreign Application Priority Data

Aug. 6, 1997 (GB) ............................................. 9716664

(51) Int. Cl.⁷ ................................................. C12Q 1/68
(52) U.S. Cl. .................. 435/6; 435/5; 435/6; 435/91.1; 435/91.2; 536/23.1; 536/23.5; 536/24.3
(58) Field of Search ........................... 435/6, 91.1, 91.2; 536/23.1, 23.5, 24.3

(56) References Cited

U.S. PATENT DOCUMENTS 6,103,463 A * 8/2000 Chetverin et al. ............. 435/6

FOREIGN PATENT DOCUMENTS

| DE | 4314271 | 11/1994 |
| DE | 19513728 | 10/1996 |
| EP | 0658621 | 6/1995 |

OTHER PUBLICATIONS

Hilali et al. Molecular Biotechnology. vol. 7, 1997, pp. 207–216.*
Chou et al., "Shrimp hepatopancreatic deoxyribonuclease—purification and characerization as well as comparison with bovine pancreatic deoxyribonuclease" *Biochimica et Biophysica Acta*, 1036, 1990, pp. 95–100.
Heinemeyer et al., "A sensitive method for the detection of murine C–type retroviruses", *Journal of Virological Methods*, 63, 1997, pp. 155–165.
Hilali et al., "Decontamination of Polymerase Chain Reaction Reagents for Detection of Low Concentrations of 16S rRNA Genes", *Molecular Biotechnology*, vol. 7, 1997, pp. 207–216.
Sanyal et al., "An Effective Methods of Completely Removing Contaminating Genomic DNA from an RNA Sample to be Used for PCR", *Molecular Biotechnology*, vol. 8, 1997, pp. 135–137.
Straetkvern et al., "Characterization of a pancreatic DNas from pyloric caeca of Atlantic cod (*Gadus morhua L.*)", *Fish Physiology and Biochemistry*, 9:439–451, 1992.

* cited by examiner

*Primary Examiner*—W. Gary Jones
*Assistant Examiner*—Janell E Taylor
(74) *Attorney, Agent, or Firm*—Dorsey & Whitney LLP

(57) ABSTRACT

The present invention provides a method of removing nucleic acid contamination in an amplification reaction which comprises use of a thermolabile DNase and a method of preventing or reducing false positive results due to carry-over in a nucleic acid amplification reaction, said method comprising using a thermolabile DNase to degrade carried-over non-target double-stranded DNA present in the amplification reaction mixture. A thermolabile DNase from the shrimp *Pandalus borealis* has been identified which is suitable for use in the methods of the invention.

11 Claims, 7 Drawing Sheets

METHOD OF REMOVING NUCLEIC ACID CONTAMINATION IN AMPLIFICATION REACTIONS

The present invention relates to the prevention of false positive results in nucleic acid amplification reactions and in particular to prevention using a DNase. The invention also relates to a thermolabile DNase suitable for use in such a method.

Nucleic acid amplification techniques such as polymerase chain reactions (PCR's) are one of the most powerful tools available in biotechnology, allowing preparation of a large number of copies of a target sequence from a sample containing only a small amount of nucleic acid. In the case of PCR, oligonucleotide primers complementary to their respective strands of a double stranded target sequence are added to the reaction mixture containing the target sequence and free nucleotides. Thermal cycling in the presence of a DNA polymerase results in amplification of the sequence between the primers. The ability of the amplified fragments created by the PCR process to act as templates for subsequent PCR cycles results in the rapid production of a considerable quantity of the target sequence. Even a single copy of the target sequence can yield sufficient nucleic acid to allow detection by, e.g. hybridization with a labelled probe or incorporation of a $^{32}$P labelled deoxynucleotide triphosphates into the amplified segment.

Ligase amplification reaction (LAR) also known as ligase chain reaction (LCR), like PCR, uses repetitive cycles and alternating temperature to achieve an exponential increase in the number of copies of the target sequence. In this method, DNA ligase catalyses the joining of two oligonucleotides complementary to adjacent regions of one of the target DNA strands. Two other oligonucleotides complementary to the other strand can also be ligated. After denaturation, the original template strands and the two ligated pairs can act as templates for further hybridisation and ligation.

Reverse transcript PCR (RT-PCR) is an amplification method in which the single strand RNA (ssRNA) template is reverse transcribed into a complementary single stranded DNA which is used to form double strand DNA (dsDNA) which is then subsequently amplified in the normal way as a DNA PCR product. Some enzymes are capable of producing the first DNA strand and synthesising the second strand to form dsDNA and others are specific for just one of the two steps.

The ability of these techniques to amplify minute quantities of a target sequence makes them highly susceptible to contamination by target sequences which may be carried over from previous amplification reactions in reagents, pipetting devices, laboratory surfaces, gloves or aerosolization. Aerosols can occur by disturbing a solution such as during a spill or even by disturbing the small amount of material on a container surface such as the residue on the inner surface of a cap of a plastic tube which can be aerosolized when the tube is opened. When the sample nucleic acid is being investigated for medical diagnostic or forensic reasons, the impact of false-positive results caused by the accidental introduction into the reaction mixture of nucleic acid which may comprise the target sequence, known as carry-over, can be far-reaching.

A number of techniques for preventing or limiting the effects of carry-over have been developed. These include nested primers, primers which anneal to the target sequence inside the annealing boundaries of the two primers used to start PCR (K. B. Mullis et al. Cold Spring Harbour Symposia Vol. LI, pp 263–273, 1986). The shorter PCR amplified product of the nested primers cannot anneal with the starting primers so if it is this product which is carried over, the use of the starting primers will not amplify this carry-over. However, the carry-over has not been removed and if the same nested primers are used in a subsequent PCR, the previously amplified product of the nested primers will be amplified.

Recently, methods have been developed which involve incorporation of the nucleotide deoxyuridine triphosphate (dUTP) into amplified nucleic acid sequences in place of thymidine triphosphate (TTP). As deoxyuridine (dU) is not normally found in naturally-occurring DNA, this nucleotide distinguishes previously produced amplicons from new target sequences. Prior to the commencement of a further amplification reaction, the amplification reaction mixture can be treated with the enzyme uracil DNA glycosylase (UDG) which removes the uracil base, leaving the sugar-phosphodiester backbone intact producing an abasic site in single strand (ss) and double strand (ds) DNA (U.S. Pat. No. 5,418,149). The temperature of the amplification reaction mixture is elevated to cleave the DNA at the abasic sites which results in degradation of the carry-over. This method too is not without problems, as the introduction of dUTP in the amplification product can interfere with subsequent analysis of the product e.g. by restriction enzyme cleavage. Also, the UDG is not irreversibly inactivated at high temperatures. The temperature steps used in the amplification reaction must be above 54° C. and the reaction vessel must be kept at high temperatures or immediately frozen, to prevent the newly produced amplifications which will also contain uracil from being degraded.

It has also been suggested that individual reaction mixtures be treated prior to addition of the target DNA and Taq DNA polymerase with DNaseI or restriction endonucleases that cut internal to the pair of amplification primers thus preventing amplification of contaminating DNA (Furrer et al. Nature. Vol. 346 page 324, 1990). This method requires a decontamination time of 30 minutes and in order to inactivate the DNaseI or restriction endonuclease after decontamination, the reaction mixture is boiled. Because of this boiling step, it is necessary to add the Taq DNA polymerase after decontamination which represents a further risk of the introduction of carry-over into the pre-amplification mixture. Primer concentrations of 1 $\mu$M are used in this method.

There thus remains a need for a method which can simply and efficiently prevent false positive results due to carry-over in nucleic acid amplification reactions.

A new DNase ie. DNA-degrading enzyme, has been isolated and purified which has been found by the inventors to exhibit characteristics which make it suitable for use in the elimination or reduction of carry-over. In particular, the DNase is thermolabile, being irreversibly inactivated at high temperatures. As with all DNases, the thermolabile DNase of the invention digests dsDNA by cleaving the phosphodiester links of the sugar phosphate nucleic acid backbone.

Thus, according to the present invention, there is provided a method of removing nucleic acid contamination in an amplification reaction which comprises use of a thermolabile DNase.

The thermolabile DNase is thus used to degrade double stranded non-target DNA present in the amplification reaction mixture. Thereby, non-specific amplification may be reduced or avoided.

In particular, the method involves contacting the amplification reaction mixture with a thermolabile DNase under conditions which permit digestion of any double stranded DNA therein; heating said reaction mixture to inactivate said DNase and thereafter bringing said mixture into contact with said target nucleic acid to be amplified. The target nucleic acid (ie. the template for amplification) may simply be added to the mixture or a barrier separating the template from the remainder of the amplification reaction, removed.

Alternatively viewed, this aspect of the invention provides use of a thermolabile DNase in removing nucleic acid contamination in an amplification reaction mixture.

As mentioned above, the invention has particular utility in preventing or limiting carry-over, and in particular in preventing or reducing false positive results due to carry-over.

In a further aspect the invention also provides a method of preventing or reducing false positive results due to carry-over in nucleic acid amplification reactions, said method comprising using a thermolabile DNase to degrade carried-over non-target double-stranded DNA present in the amplification reaction mixture.

The term "amplification reaction" refers to any in vitro means for increasing the number of copies of a target sequence of nucleic acid. Preferably, methods will involve "thermal cycling", ie. involving high temperature cycling. Methods include but are not limited to PCR and modifications thereto, LAR or LCR and RT-PCR. Methods may result in a linear or exponential increase in the number of copies of the target sequence.

The target nucleic acid may be DNA or RNA depending on the selected amplification method. For example, for PCR a target RNA may be first transcribed into DNA using a reverse transcriptase enzyme (RT-PCR).

The term 'amplification reaction mixture' refers to any solution, generally aqueous, comprising the various reagents used to amplify a target nucleic acid. These include enzymes, aqueous buffers, salts and nucleoside triphosphates. The term refers to mixtures which contain all the necessary components for carrying out a successful amplification reaction and to mixtures which are incomplete and therefore contain only some of the required components.

The term "DNase" refers to an enzyme which hydrolyzes a phosphodiester bond in the DNA backbone and is not nucleotide sequence specific.

The term "removing nucleic acid contamination" is intended to cover both the prevention and reduction of nucleic acid contamination.

The term 'carry over' is used to describe any nucleic acid which is accidentally or unintentionally introduced into a reaction mixture, in particular target sequences carried over from previous amplification reactions.

The term 'false positive result' refers to a result which appears to show that the nucleic acid sample under investigation contains the target sequence but wherein the amplified product is derived from carry-over. Clearly, the reduction in false positive results which the invention provides is particularly advantageous in the forensic and diagnostic fields. The methods of the invention enable the specificity of nucleic acid amplification to be increased.

The term 'thermolabile DNase' refers to a DNase which is at least substantially irreversibly inactivated at high temperatures suitable for amplification reactions. The DNase is thus effectively substantially irreversibly inactivated after 5 minutes at 94° C., preferably after 2 minutes at 94° C.

By "substantially inactivated" is meant that on heating, the enzyme is at least 95% inactivated, preferably 98% inactivated. Preferably, the enzyme is 100% inactivated after 3 minutes heating. Even when the temperature of the reaction mixture returns to room temperature, the DNase does not regain its activity and there is substantially no residual activity; specifically, less than 5%, preferably less than 2%, most preferably no detectable DNase activity remains. Such a thermolabile DNase enzyme itself constitutes a further aspect of the invention.

This aspect of the invention thus provides a thermolabile DNase enzyme which is substantially specific for double-stranded DNA and which is substantially irreversibly inactivated by heating at 94° C. for 5 minutes.

The thermolabile DNase acording to the invention can be considered to be cold adapted as it is active at temperatures (e.g. room temperature) at which thermophilic DNA polymerase is not. Linear double stranded DNA and supercoiled circular DNA are both substrates of the enzyme according to the invention. The enzyme has little or no activity for single stranded DNA such as amplification primers. Specifically, no detectable activity for single stranded DNA has been observed following incubation of the enzyme (0.1 U/$\mu$l enzyme preparation) with a single stranded product for 30 minutes at room temperature.

The enzyme is substantially irreversibly inactivated at high temperatures such as those used during normal cycling in amplification reactions. These characteristics permit the inclusion of the DNase within the reaction mixture comprising primers, nucleotides, DNA polymerase and buffers and the rapid degradation of all carry-over material at room temperature. Advantageously, the thermolabile DNase of the invention is fully functinal in a complete amplification reaction mixture, and is compatible with standard in vitro amplification reactants and conditions. Preferably, the DNase is able to degrade all the carry-over within 5 minutes at room temperature, most preferably, within 2.5 minutes.

The temperature of the reaction mixture can then be raised for a short time, advantageously to 94° C. for 1–2 minutes, which irreversibly inactivates the thermolabile DNase. The nucleic acid samples to be amplified and analysed (ie. the target nucleic acid) can then be added and amplification begun. Even when the temperature of the reaction mixture drops during the thermal cycling and after amplification, the copies of the target sequence will not be degraded because the DNase has been irreversibly inactivated. It is a particular advantage of the present invention that the DNA polymerase can be included in the reaction mixture while the decontamination and subsequent inactivation steps take place. This is as a result of the fairly gentle conditions which result in inactivation of the DNase (eg. 94° C. for 1–2 minutes) so a further potential source of contamination is removed.

Although it is clear that any thermolabile DNase having the characteristics described above may be suitable for use in the methods according to the invention, a particular DNase derived from the shrimp (*Pandalus borealis*), whose isolation is described in Example 1, forms another aspect of the present invention.

Also included within the scope of the present invention are enzyme variants which are functionally equivalent to native thermolabile DNase's but which have been modified by genetic or chemical manipulation. Active fragments may also be used. For example, sequence modifications of the *Pandalus borealis* enzyme are encompassed within the invention. Techniques for modification of polypeptide or nucleotide sequences are well known and standard in the art, and it is known for example to obtain such modified variants by amino acid substitution, addition or deletion.

The use of the DNase from *Pandalus borealis* in the decontamination methods described herein represents a particularly preferred embodiment of the invention.

Advantageously, an enzyme which is suitable for use in decontamination techniques should not significantly inhibit intended amplification nor affect the nature of the final amplified product eg. by interfering with subsequent analysis. The particular thermolabile DNase of the present invention does not inhibit intended amplification because it is inactivated at the elevated temperatures of the amplification reaction or can be inactivated in a separate step prior to commencement of the amplification. Also, the DNase does not require modified nucleotides, and thus the amplified product is identical to conventional amplification products and can be analysed in the same way. In other words, in the method of the present invention, unlike the UDG—decontamination method, the decontaminating enzyme does not affect the nature of the final amplified product.

Unlike the decontamination system described by Furrer et al. (supra) the methods according to the present invention have the further advantage that they permit the use of low primer concentrations, typically 0.05–0.2 $\mu$M.

The enzyme should also be capable of removing suitable amounts of carry-over from a reaction mixture, usually fg- or pg-levels but preferably up to 1 ng. 1 unit (U) of the DNase of the present invention can remove 1 ng of a 507 bp dsDNA, ie. $2 \times 10^9$ molecules during 2.5 minutes at room temperature in a 1×PCR buffer of Taq polymerase, (e.g. according to the Kunitz assay as described in the Examples). Thus enzymes for use in the methods according to the invention may ideally have a decontamination efficiency of at least $1 \times 10^9$ molecules per unit of enzyme, preferably $2 \times 10^9$ molecules per unit of enzyme. Removal of carry-over need not be by total degradation of the nucleic acid. The decontamination system described by Furrer et al. (supra) had a decontamination efficiency of only $2 \times 10^3$ molecules/U. The efficiency of both decontamination systems in actual PCR reaction mixtures are likely to be somewhat lower than the optimum values given above.

$10^2$ target molecules are sufficient for a successful PCR amplification, see e.g. Example 2, and $2 \times 10^9$ molecules are prevented from amplification by the DNase of the present invention. Thus enzymes for use in the methods according to the invention may reduce the amount of carry over which could potentially be amplified by a factor of at least $2 \times 10^7$.

A method for the isolation and purification of the thermolabile DNase from *Pandalus borealis* represents a further aspect of the present invention. Thus, in this aspect the invention provides such a method, comprising obtaining an extract from *Pandalus borealis*, containing the DNase, and subsequently separating the DNase from said extract.

The DNase enzyme may be separated, or isolated, from the extract using any of the purification techniques for proteins, known in the art and widely described in the literature or any combination thereof. Such techniques may include for example, precipitation, ultrafiltration, dialysis, various chromatographic techniques, eg. gel filtration, ion-exchange chromatography, FPLC, affinity chromatography, electrophoresis, centrifugation etc.

Likewise an extract of *Pandalus borealis* may also be prepared using techniques well known in the art, eg. homogenisation, freeze-thawing etc. The DNase of *Pandalus borealis* may be found in the digestive gland (hepatopancreas) of the shrimp and this may be separated/extracted if desired and used as the source the enzyme for purification. Other species living in cold environments may also be a source of suitable thermolabile DNases.

It has been found that a purification protocol based on a combination of ion exchange chromatography and chromatography on a Red-sepharose column (Pharmacia Biotech, Sweden) may readily be used to isolate the enzyme.

More particularly, the extract may be subjected to ion-exchange chromatography and the protein eluted with a NaCl gradient. The fractions containing DNase activity may be dialysed and then applied to an affinity column before final elution with NaCl.

A particularly convenient source of the *Pandalus borealis* DNase is the so-called "shrimp processing water". Shrimp processing water occurs as a "by-product" of the large scale processing of shrimps for peelinig and consumption. The shrimp catch is initially frozen, and then for subsequent processing it is thawed by adding fresh water at low temperatures. The frozen digestive gland breaks when the frozen shrimps are thawed and liberates its enzyme content into the water used during the thawing process. This thawing water may conveniently be re-circulated and the same water may thus be used for the thawing of a large number of shrimps, which can lead to the build-up and concentration of the liberated enzymes. This shrimp processing water will thus contain the thermolabile DNase and other liberated enzymes and provides a convenient extract which can be purified to yield the DNase.

Ideally, a reaction vessel should be opened as few times as possible prior to commencement of amplification to reduce the opportunities for contamination. If the nucleic acid sample to be amplified were present in the reaction vessel during the decontamination process and therefore did not have to be added after inactivation of the DNase, this would be highly advantageous. The following modifications to routine amplification protocols which mean that the nucleic acid sample need not be added after inactivation of the DNase comprise further aspects of the invention. For example, a double stranded DNA sample can be denatured eg. by boiling to render it single stranded and therefore not susceptible to DNase degradation, before addition to the DNase-containing reaction mixture. The single stranded DNA sample is preferably stored on ice before addition to the reaction mixture.

In an alternative embodiment, target nucleic acid eg. a double stranded DNA sample is separated from the main reaction-mixture by a material such as wax (Perkin Elmer) which melts at the high temperatures at which the DNase is inactivated. Once the wax partition has melted, the DNA sample can come into contact with the rest of the reaction mixture and amplification of the target sequence begun. Such a method is known as 'hot-start' and a variety of 'hot-start' procedures are known in the art.

The present invention also provides kits which comprise at least a thermolabile DNase according to the invention. The kits may also contain all the necessary reagents, buffers, enzymes etc. to carry out nucleic acid amplification reactions. More particularly, the kits may contain nucleotide triphosphates, oligonucleotide primers, a DNA polymerase, preferably a thermostable polymerase such as Taq polymerase or in the case of LAR, a DNA ligase. The DNase may be provided in one compartment together with a DNA polymerase or LCR ligase.

The present invention also provides a method of in vitro amplification of a target nucleic acid, characterised in that said method includes a step of treating the reaction mixture or individual components thereof with a thermolabile DNase prior to commencement of the actual amplification reaction.

Conveniently such a method will involve or be based on the PCR. PCR methods are of course now standard in the art, and may be effected using any known or standard reagents and techniques.

In a typical PCR reaction protocol, the decontamination step may simply involve incubating the amplification reaction mixture containing the DNase for a short period of time, for example 1 to 10 minutes at room temperature, conveniently 2 to 5 minutes. The time of this incubation is not critical and may vary depending on the exact DNase and level used, and the other components of the reaction system. The temperature may be any temperature at which the enzyme is active ie. below the inactivation temperature, but room temperature is convenient.

Such a reaction mixture may, as mentioned above, contain all the necessary reactants for the amplification reaction, aside from the template ie. the target nucleic acid to be amplified.

A typical representative PCR amplification reaction mixture may for example include:

| Component | Final Concentration |
| --- | --- |
| dATP | 50–200 $\mu$M |
| dCTP | 50–200 $\mu$M |
| dGTP | 50–200 $\mu$M |
| dTTP | 50–200 $\mu$M |
| Primer 1 | 0.05–0.2 $\mu$M |
| Primer 2 | 0.05–0.2 $\mu$M |
| AmpliTaq ® DNA polymerase | 1–2.5 Units |
| *Pandalus borealis* ds DNase | 0.05–0.2 Units |
| MgCl$_2$ | 1.0–3.0 mM |
| PCR Buffer | 1X |
| Sterile distilled water | to final 50–100 $\mu$l |
| Experimental template (to be added after inactivation of DNase) | 50 pg-100 ng |
| Total Mix | 50–100 $\mu$l |

In the above representative example, any combination of sterile distilled water and experimental template volumes can be used as long as the total volume of the reaction (including buffer, dNTPs, primers, enzymes and MgCl$_2$ solutions) equals 50–100 $\mu$l. However, alternative final volumes may be used according to choice, to achieve e.g. similar or other desired final concentrations of reactants. Any convenient or commercially available PCR buffer may be used. A suitable 10×PCR buffer may be 100 mM Tris-HCl, pH 8.3, and 500 mM KCl. A PCR buffer may be purchased from Perkin-Elmer Cetus.

Depending on the level of potential contamination, the amount of DNase needed may vary. With a short incubation step (0–10 minutes at room temperature), 0.1 Units/50 $\mu$l reaction mixture is generally more than sufficient. 0.05 to 0.2 units/50 $\mu$l reaction mixture is suitable and an activity of approximately 0.1 units/50 $\mu$l reaction mixture e.g. 0.08 to 0.12 Units/50 $\mu$l reaction mixture)is preferred. At a concentration of 1 Unit/50 $\mu$l reaction mixture some ssDNase activity is observed and therefore the activities listed above are preferred, particularly where contamination is double-stranded and target single-stranded nucleic acid. One unit of enzyme is defined as the amount that in the Kunitz assay (Kunitz M., 1950 Crystalline Deoxyribonuclease II. Digestion of Thymus Nucleic Acid. The Kinetics of Reaction: J. Gen. Physiol., 33 363–377) increases the absorbtion at 260 nm by 0.001 per minute.

It has for example been found that 2 $\mu$l of a DNase enzyme preparation prepared according to Example 1 may be used for a 50 $\mu$l reaction volume, the reaction volume thus containing approximately 0.1 U of enzyme activity. After incubation, the DNase is inactivated by heating the reaction mixture. Conveniently this may be achieved by heating in the first PCR cycle.

Optimal performance of the PCR process is influenced by choice of temperature, time at temperature, and length of time between temperatures for each step in the cycle. A typical cycling profile for utilizing DNase to degrade contaminating ds DNA prior to PCR amplification of freshly added target nucleic acid is as follows: (a) 0 to 10 minutes of DNase incubation at room temperature; (b) 2 minutes of DNase inactivation at 94° C.; (c) addition of template; 1 minute of DNA melting at 94° C.; (d) 15 seconds of primer annealing at 50–65° C.; (e) 30 seconds of primer extending at 72° C.; (f) 10 seconds of DNA melting at 94° C.; and steps (d)–(f) are repeated as many times as necessary to obtain the desired level of amplification.

The invention will now be described by way of non-limiting Examples with reference to the following figures in which.

EXAMPLE 1

Isolation of Shrimp (*Pandalus borealis*) DNase

Figure 1:
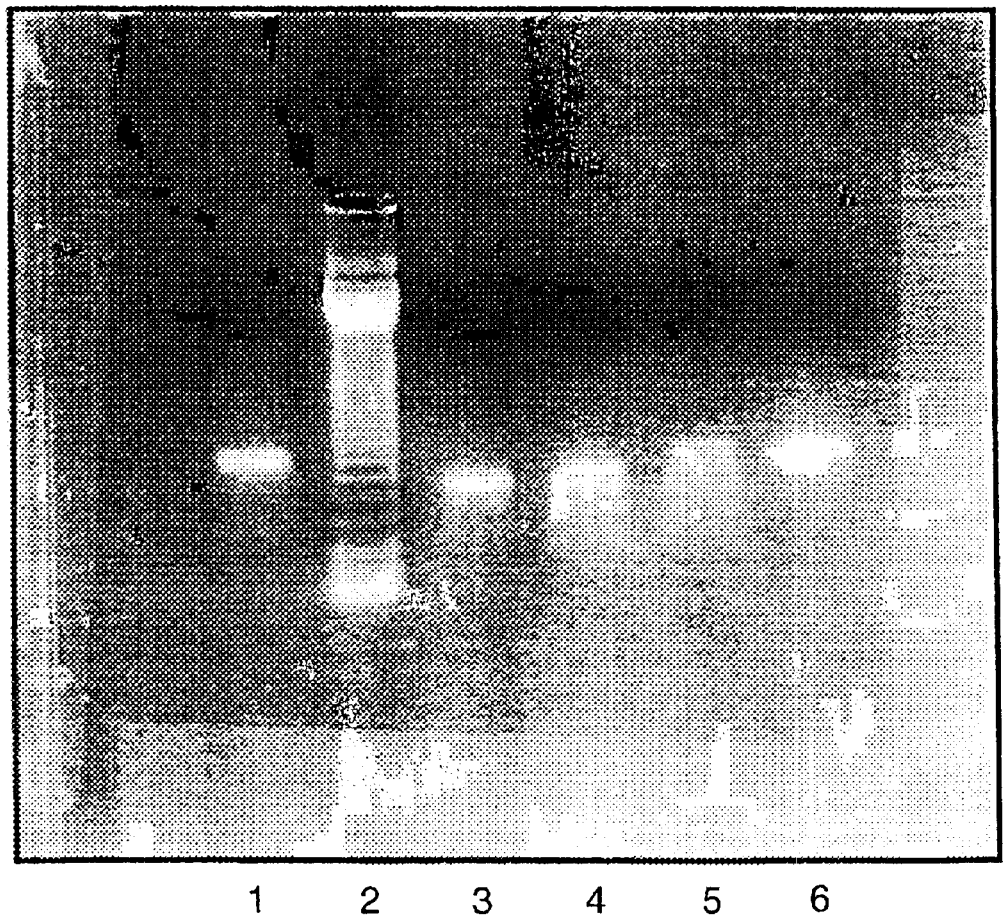
FIG. 1 is a photograph of an agarose gel showing activity of the thermolabile DNase against PCR DNA product.

The thermolabile DNase is obtained from shrimp (*Pandalus borealis*) processing water, a by-product of the shrimp fishing industry. Most of the catch is frozen on board the fishing vessels. When processed in land based factories, the frozen blocks are thawed by passing them on a conveyor under sprinkling by temperated fresh water (less than 15° C.). The frozen digestive gland of the shrimp (hepatopancreas) will break and liberate different enzymes into the water. This water is recirculated so that the same water can be used for thawing of approximately 10–12 tonnes of shrimps each day; thus the concentration of enzymes in the water will increase during the day. This processing water is the source of the shrimp DNase.

Shrimp processing water was clarified by centrifugation two times 10,000×g for 20 minutes at 4° C., followed by ultraconcentration using a nominal molecular weight cut-off membrane of 10 kDa. The concentrate was run through a Q-sepharose ion-exchange chromatography column, equilibrated in 0.05M sodium acetate buffer, pH 8.0, containing 5 mM MgCl$_2$. The column was washed with 0.3M NaCl and the protein eluted with a gradient of 0.3M to 1.5M NaCl. Fractions containing DNase activity were collected by elution with 0.7–1.1M NaCl. The pooled fractions containing DNase activity were dialysed against 0.01M sodium acetate, pH 8.0, with 5 mM MgCl$_2$. The dialysed material was applied to a Red-Sepharose column (Pharmacia Biotech, Sweden) followed by extensive washing with 0.3M NaCl. Finally, bound DNase was eluted with 1.5M NaCl.

Sodium chloride was removed from the DNase prior to assay. The DNase activity is assayed according to the procedure of Kunitz (Kunitz, M., 1950, Crystalline Deoxyribonuclease, II, Digestion of Thymus Nucleic Acid. The Kinetics of Reaction. J. Gen. Physiol., 33, 363–377). 50 µl of enzyme preparation is added to 200 µg calf thymus DNA in 100 mM sodium acetate, pH 5.0, 5 mM $MgCl_2$, in a final volume of 1 ml. The mixture is incubated at 37° C. After 20 minutes incubation, 0.5 ml ice-cold 12% $HClO_4$ is added and thoroughly mixed and left on ice for 20 minutes. The tubes are centrifuged on full speed in an Eppendorf centrifuge for 5 minutes. Absorbtion at 260 mm is determined from which the Kunitz units are calculated. 1 U=0.001 $OD_{260}$ increase×$min^{-1}$

EXAMPLE 2

PCR Amplification of Aeromonas salmonicida GCAT

Gene: GCAT (glycero-phospholipid-cholesterol acetyltransferase), 1176 bp.

GenBank accession number X70686.

Forward primer GCAT-1: 5'-TTGGGGTTGATCGCGCT GA-3' Identical to gene positions 65–83

Reverse primer GCAT-2: 5'-CCCAGATCCGGCAGGTT GA-3' Reverse complementary to positions 552–571

Template: A. salmonicida genomic DNA.

PCR mixture:

0.5 µM of each primer
1 mM $MgCl_2$
50 µM of each dNTP's
10 pg template DNA (correspnds to approx. 100 genomic copies)
1×PCR buffer
1 U Taq polymerase
$H_2O$ to final 100 µl PCR thermal cycles:
1×; 94° C. 4 min
35×; 94° C. 10 sec
  55° C. 15 sec
  72° C. 15 sec
1×; 72° C. 5 min

EXAMPLE 3

Test of Shrimp DNase Activity on PCR DNA Product

Materials, used in this and subsequent examples:

Shrimp DNase from Pandalus borealis (approx. 0.1 Unit/50 µl reaction mixture), see Example 1

Taq buffer and Taq-polymerase(Perkin-Elmer Cetus)

123 bp MW marker (Gibco)

PCR product of GCAT from A. salmonicida generated using GCAT1 and 2 primers, see Example 2.

Thermal cycler (2400 Perkin-Elmer Cetus)

300 ng GCAT PCR-product (507 bp) was mixed with 2 µl concentrated, partly purified DNase from shrimp in 2 mM $MgCl_2$, 1×Taq-buffer to a final volume of 50 µl. Samples were immediately placed at 37° C. in a Thermal cycler machine. 15 µl samples were drawn at 2, 7 and 15 minutes and loaded on a 1.3% agarose gel.

1µl concentrated, partly purified shrimp DNase was mixed in a total of 15 µl 2 mM $MgCl_2$, 1×Taq buffer. The sample was subjected to 94° C. for 2 minutes with subsequent transfer to 37° C. using the Thermal cycler. A 15 µl sample was drawn after 15 minutes and loaded on the 1.3% agarose gel.

Samples were run in 1×TBE for 30 minutes in the presence of EtBr before being photographed on a UV-transilluminator. See FIG. 1 in which:

Lane:
1—GCAT PCR product from A. salmonicidae
2—123 bp MW markers
3—GCAT PCR-product incubated with DNase at 37° C. for 2 minutes
4—GCAT PCR-product incubated with DNase at 37° C. for 7 minutes
5—GCAT PCR-product incubated with DNase at 37° C. for 15 minutes
6—GCAT PCR-product incubated with DNase at 37° C. for 15 minutes, after heat treatment of DNase.

The DNase was tested for activity on a specific PCR product (approximately 100 ng of GCAT, 507 bp) and shown to have significant ability to degrade the double stranded (ds) DNA after 15 minutes at 37° C. in 1×Taq-polymerase assay buffer including 2 mM $MgCl_2$, the buffer system used in all Examples. 2 minute preincubation at 94° C. was shown to inactivate the DNase.

EXAMPLE 4

Test of Thermolabile Shrimp DNase in Decontaminating Carry-over Products of PCR Reactions Materials:

GCAT PCR-product from A. salmonicidae

Taq-polymerase

DNase from shrimp, concentrated and partly purified

Primers (oligonucleotides GCAT1 and 2), dNTP mix, $MgCl_2$, Taq-buffer and Taq-polymerase, concentrations as before, were mixed in a total volume of 218 µl and distributed to 6 PCR tubes. $H_2O$ was added so the final volume was be 50 µl per tube. 1 ng GCAT PCR product was added to tubes 3, 4 and 6 imitating carry-over. 2 µl DNase was added to tubes 2, 4, 5 and 6. The tubes were placed in the Thermal cycler at 37° C. for 15 minutes. The cycler machine was activated on the following PCR program;

| 1 cycle, initial heating, | 94° C., 4 minutes |
| 35 cycles | 94° C., 10 seconds |
| | 60° C., 15 seconds |
| | 72° C., 15 seconds |

Figure 2:
FIG. 2 is a photograph of an agarose gel showing the effect of the DNase on inhibiting amplification of carry-over contamination and showing DNase inactivation at high temperatures.

1 ng GCAT PCR-product template was added to tubes 1, 5 and 6 after 2 minutes of the initial heating step at 94° C. After completion of the PCR cycles, 15 µl samples from each tube were subjected to electrophoresis in a 1.3% agarose gel (1×TBE) and stained with EtBr. See FIG. 2 in which:

| Lanes: | Carry-over | DNase | Template | PCR-production |
|---|---|---|---|---|
| 1-GCAT template, no carry over, no DNase | − | − | + | + |
| 2-DNase, no template, no carry-over | − | + | − | − |
| 3-GCAT carry-over, no template, no DNase | + | − | − | + |

-continued

| Lanes: | Carry-over | DNase | Template | PCR-production |
|---|---|---|---|---|
| 4-GCAT carry-over, DNase, no template | + | + | − | − |
| 5-GCAT template, DNase, no carry-over | − | + | + | + |
| 6-GCAT carry-over, DNase, GCAT template | + | + | + | + |

PCR reactions of mixtures including 1 ng PCR product and DNase showed that DNase treatment prevented amplification of the contaminating PCR-product. Addition of the PCR-product after 2 minutes of the initial heating step resulted in amplification, demonstrating that a) the DNase did not degrade single stranded oligonucleotide PCR primers; b) DNase treatment was successfully preventing amplification of carry-over products; and c) the DNase activity is sufficiently destroyed by heating at 94° C. for 2 minutes to not inhibit amplification of DNA (1 ng PCR-product) added subsequently.

EXAMPLE 5

Test of Shrimp DNase Activity on PCR Carry-over vs. Temperature

Figure 3:
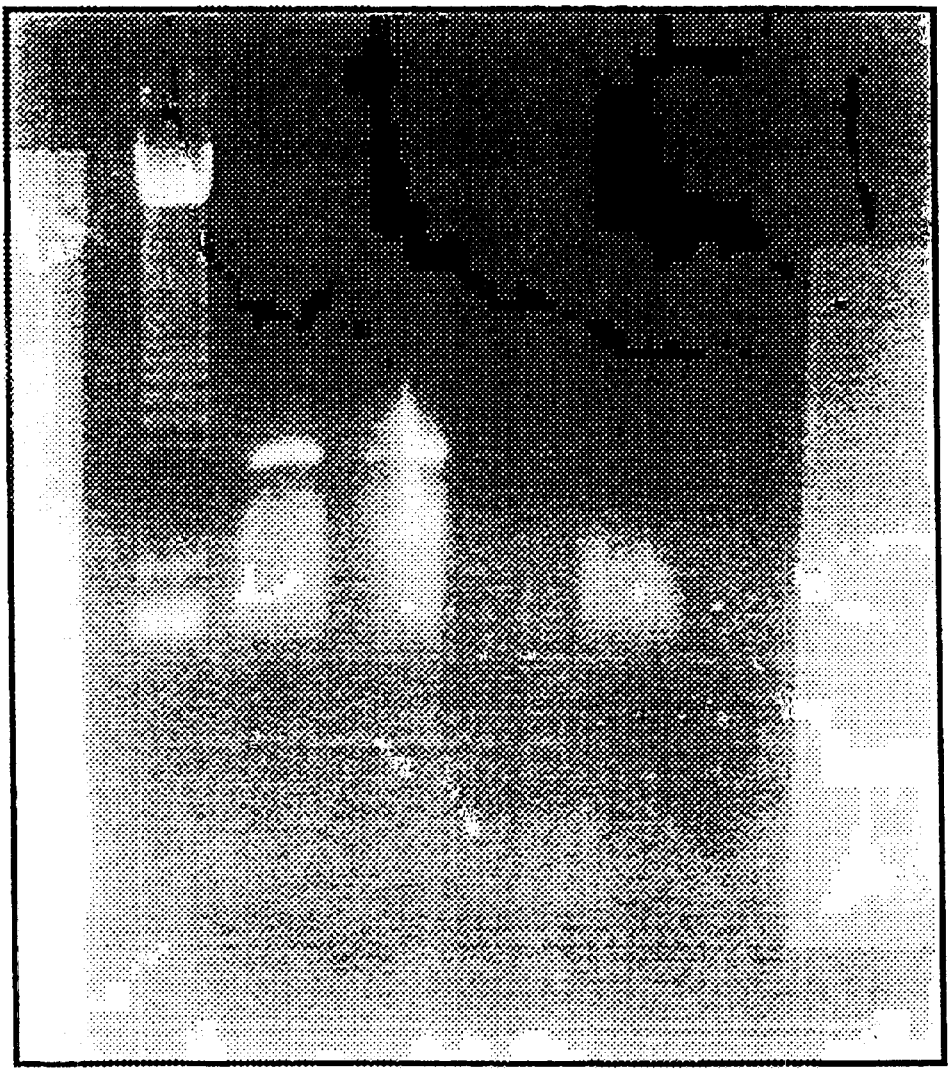
FIG. 3 is a photograph of an agarose gel showing DNase activity at different temperatures.

PCR reaction mixture including 1 ng GCAT PCR product was set up as described in previous Examples and dispensed into 4 tubes. 2 µl of purified DNase (further purified from the DNase of Example 3 and 4 using a size-exclusion chromatography column (Superose 12; Pharmacia, equilibrated with 50 mM Tris-HCl, pH 8.1, 5 mM $MgCl_2$ and 150 mM NaCl was added to tubes 2, 3 and 4. Tubes were incubated for 15 minutes at 12° C. (thermal cycler), 22° C. (room temperature) and 37° C. (water-bath) respectively. All 4 tubes were transferred to hot-start in the Thermal cycler and PCR reactions were carried out as before. 10 µl samples from the final PCR reactions were run on 1.3% agarose gels and visualized. See FIG. 3 in which:

Lanes:
  0—MW marker
  1—PCR reaction, no DNase
  2—PCR reaction, DNase-treatment 12° C.
  3—PCR reaction, DNase-treatment 22° C.
  4—PCR reaction, DNase-treatment 37° C.

Degradation tests showed that the DNase is not active at 12° C. and that the DNase activity is higher at 22° C. than at 37° C.

EXAMPLE 6

Test of Shrimp DNase Activity on PCR Carry-over vs. Time

Figure 4:
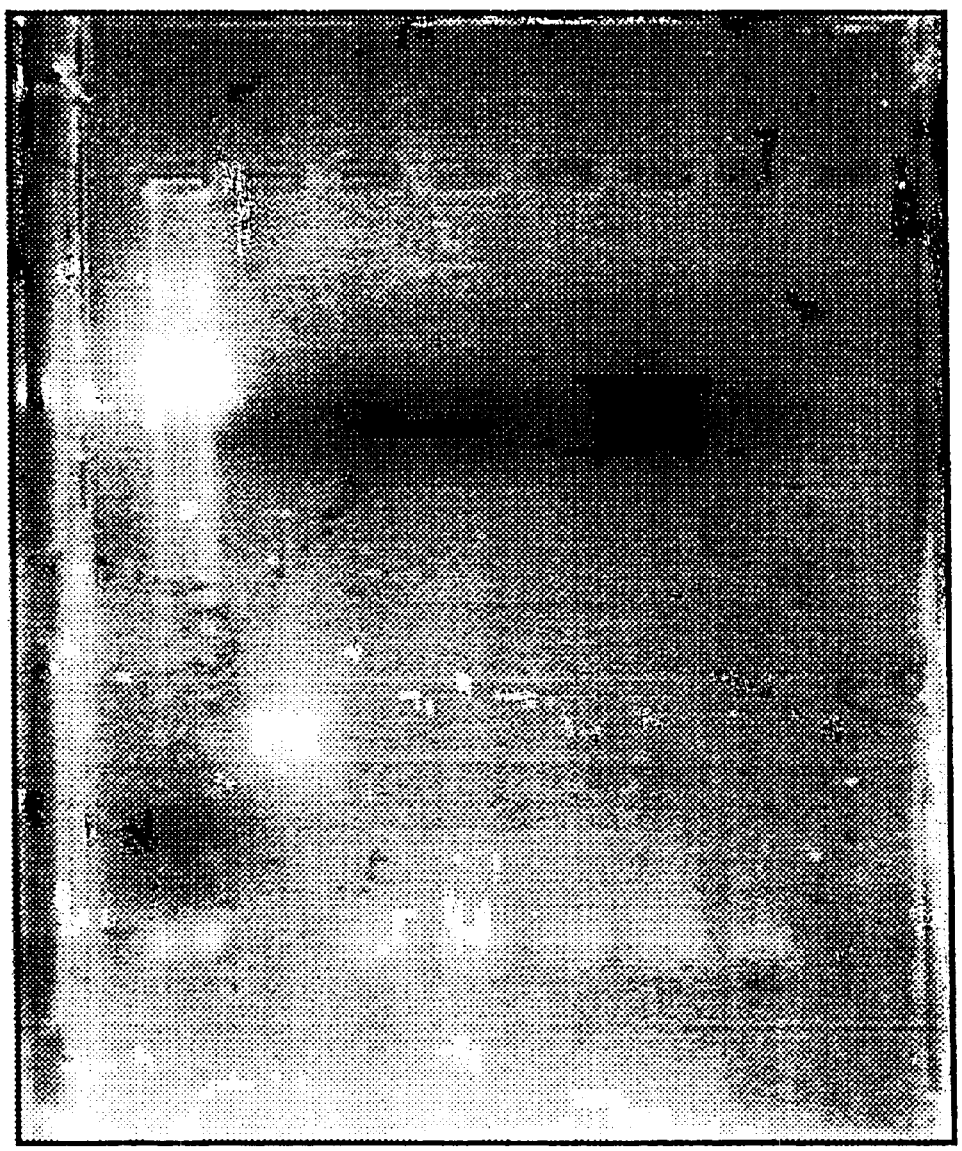
FIG. 4 is a photograph of an agarose gel showing the time required by the DNase to degrade a PCR product carry-over in a subsequence PCR.

PCR reaction mix including 6 ng GCAT PCR product was set up and dispensed into 6 tubes. 2 µl DNase was added to tubes 2, 3, 4 and 5, and the tubes were incubated at 22° C. The tubes were transferred to the thermal cycler for hot-start after 2.5, 5, 7.5, 10 and 15 minutes (tubes 2, 3, 4, 5 and 6 respectively). PCR reactions were carried out as described in previous Examples. 10 µl PCR product samples from each tube were subjected to agarose gel electrophoresis. See FIG. 4 in which:

Lanes:
  0—123 bp ladder MW marker
  1—PCR reaction, no DNase
  2—PCR reaction, DNase-treatment 2.5 minutes
  3—PCR reaction, DNase-treatment 5 minutes
  4—PCR reaction, DNase-treatment 7.5 minutes
  5—PCR reaction, DNase-treatment 10 minutes
  6—PCR reaction, DNase-treatment 15 minutes Time versus activity tests on functional PCR reactions showed that 2.5 minutes at 22° C. is sufficient to inhibit amplification of 1 ng PCR-product incubated in the presence of DNase.

EXAMPLE 7

Test of Shrimp DNase Inactivation During Initiation of PCR Reaction

Figure 5:
FIG. 5 is a photograph of an agarose gel showing the temperature and time required to inactivate the DNase.

PCR reaction mix including 1 ng GCAT PCR product was set up and dispensed into 5 tubes. 2 µl of partly purified shrimp DNase was added to each of 4 tubes (2–5) and the tubes were left at 22° C. for 5 minutes. The tubes were transferred to the Thermal cycler and the PCR cycling profile was started. To 3 tubes were added 1 ng GCAT PCR product when the temperature reached 70° C. (tube 3), 94° C. (tube 4) or 1 minute after reaching 94° C. (tube 5) in the initial heating step. After completed PCR cycles, 10 µl samples were analyzed on agarose gel. See FIG. 5 in which:

Lanes:
  0—123 bp ladder MW marker
  1—PCR reaction with 1 ng GCAT-product, no DNase
  2—PCR reaction with 1 ng GCAT-product, with DNase
  3—PCR reaction with 1 ng GCAT-product, with DNase, template added at 70° C.
  4—PCR reaction with 1 ng GCAT-product, with DNase, template added at 94° C.
  5—PCR reaction with 1 ng GCAT-product, with DNase, template added after 1 minutes at 94° C.

Decontamination tests showed that the PCR mix including DNase had to be at 94° C. for at least 1 minute before addition of template DNA (1 ng PCR product) to avoid substantial inhibition of PCR amplification.

EXAMPLE 8

Figure 6:
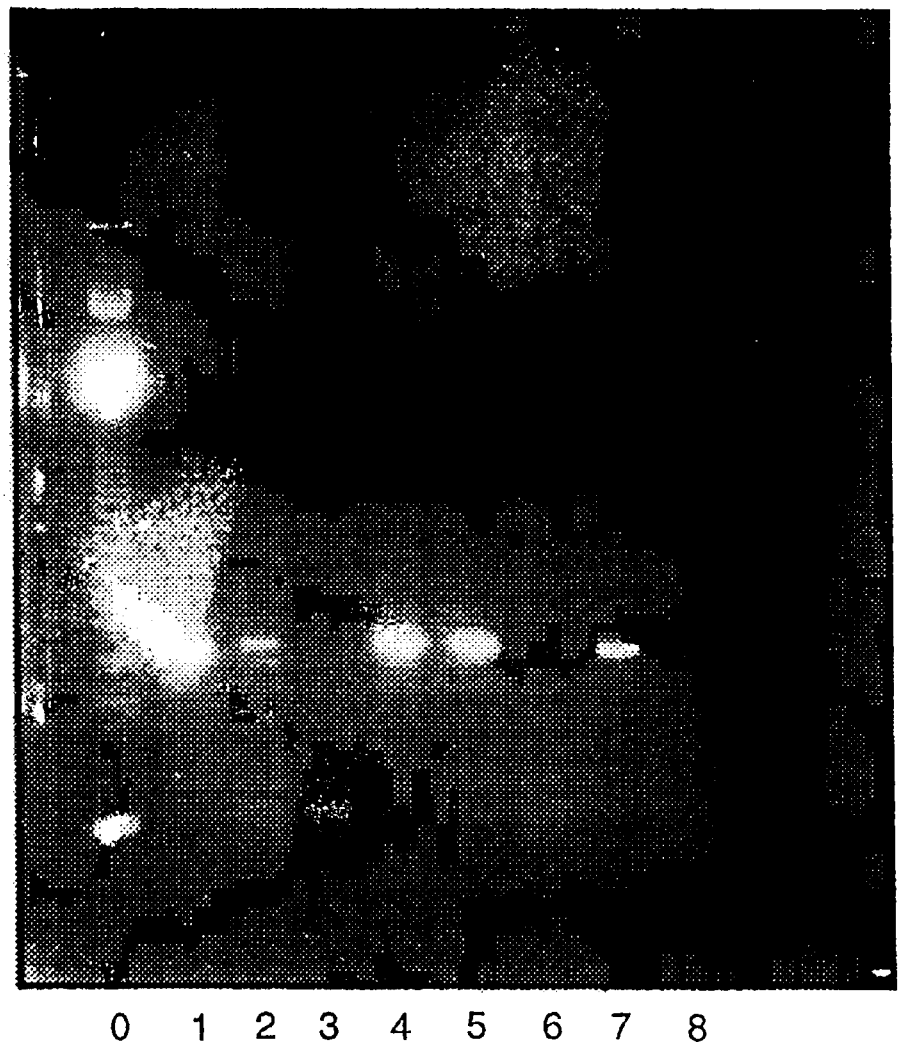
FIG. 6 is a photograph of an agarose gel showing the concentration of DNase required for decontamination of carry-over and dependence of Mg$^{2+}$ in reaction mixture.

Test of Requirements for Mg2+ and Enzyme Concentrations of Shrimp DNase for Decontamination of Carry-over Products in PCR Reactions A master PCR mix including 8 ng GCAT PCR product was distributed to 8 tubes (100 µl each). The $Mg2^+$ in each tube was adjusted (0 mM; tubes 1 and 2, 1 mM; tube 3, 2 mM; tubes 4, 5 and 6, 5 mM; tubes 7 and 8). 2 µl partly purified DNase was added to four of the tubes (2, 3, 6 and 8), and 0.1 or 0.5 µl to tubes 4 and 5. The tubes were incubated at room temperature (approx. 22° C.) for 5 minutes before being placed in a thermal cycler and subjected to the PCR cycling steps. 10 µl samples were analyzed on agarose gel. See FIG. 6 in which:

Lanes:
  0—MW standard
  1—PCR mix with 1 ng carry-over DNA, no Mg2+, no DNase
  2—PCR mix with 1 ng carry-over DNA, no Mg2+, 2 µl DNase 3—PCR mix with 1 ng carry-over DNA, 1 mM Mg2+, 2 µl DNase 4—PCR mix with 1 ng carry-over DNA, 2 mM Mg2+, 0.1 µl DNase 5—PCR mix with 1 ng carry-over DNA, 2 mM Mg2+, 0.5 µl DNase 6—PCR mix with 1 ng carry-over DNA, 2 mM Mg2+, 2 µl DNase 7—PCR mix with 1 ng carry-over DNA, 5 mM Mg2+, no DNase 8—PCR mix with 1 ng carry-over DNA, 5 mM Mg2+, 2 µl DNase 1 mM $Mg^{2+}$ is as sufficient as 5 mM $Mg^{2+}$ for the decontaminating activity of 2 µl DNase in 100 µl final solution including 1 ng carry-over PCR product. 0.1 or 0.5 µl DNase (1 and 5 µl of 10 fold diluted enzyme) is not sufficient for activity; this could be due to instability.

EXAMPLE 9

Thermolabile Shrimp DNase Activity on ss- and dsDNA

Figure 7:
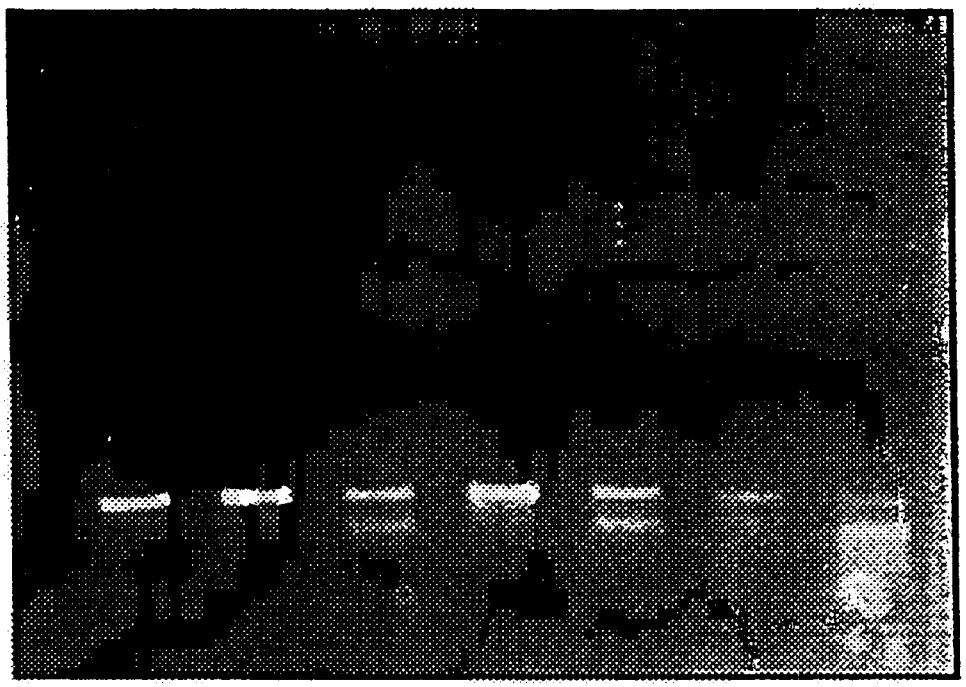
FIG. 7 is a photograph of an agarose gel showing the dsDNA specificity of DNase.

A master mix was made of 600 ng PCR product, 2 mM $Mg^{2+}$ and 1×Taq buffer to a final volume of 90 µl, and distributed between 3 tubes. Tubes 2 and 3 were subjected to boiling for 6 minutes. Tube 2 was placed for 5 minutes at 60° C. and then 5 minutes at 25° C. Tube 3 was placed directly on ice for 10 minutes after boiling. 10 µl was drawn from all 3 tubes and kept on ice. To the remaining 20 µl (approximately 200 ng DNA) in tubes 2 and 3 was added 2 µl partly purified DNase, and the tubes were incubated at room temperature for 30 minutes with withdrawal of 10 µl from each sample after 5 minutes (which were kept on ice). The samples of 10 µl were kept on ice and then analyzed on an agarose gel. See FIG. 7 in which:

Lanes:
1—Non-manipulated PCR product
2—Boiled renaturated (ds) PCR product
3—Boiled denaturated (ss and ds) PCR product
4—Boiled renaturated (ds) PCR product, DNase treatment 5 minutes
5—Boiled denaturated (ss and ds) PCR product, DNase treatment 5 minutes
6—Boiled renaturated (ds) PCR product, DNase treatment 30 minutes
7—Boiled denaturated (ss and ds) PCR product, DNase treatment 30 minutes Tests with ss- (heat denatured) and ds-DNA of a PCR product showed that the DNase has preference for dsDNA and low, if any, activity on ssDNA in the assay system used—PCR buffer conditions.

What is claimed is:

1. A method of preventing or reducing false positive results due to carry-over in a nucleic acid amplification reaction, said method comprising contacting an amplification reaction mixture with a thermolabile DNase which is substantially specific for double-stranded DNA, wherein said DNase is derived from the species *Pandalus borealis* or is a functional equivalent thereof, to degrade carried-over non-target double-stranded DNA present in the amplification reaction mixture.

2. A method as claimed in claim 1 wherein the amplification reaction is a polymerase chain reaction (PCR).

3. A thermolabile DNase which is substantially specific for double-stranded DNA, wherein said DNase is derived from the species *Pandalus borealis*, either the native enzyme or functional equivalents including active fragments.

4. A method of in vitro amplification of a target nucleic acid comprising treating the reaction mixture or individual components thereof with a thermolabile DNase which is substantially specific for double-stranded DNA, wherein said DNase is derived from the species *Pandalus borealis* or is a functional equivalent thereof, prior to commencement of the actual amplification reaction.

5. A method of removing nucleic acid contamination in an amplification reaction which comprises contacting an amplification reaction mixture with a thermolabile DNase which is substantially specific for double-stranded DNA, wherein said DNase is derived from the species *Pandalus borealis*, or is a functional equivalent thereof.

6. A method as claimed in claim 5 wherein an amplification reaction mixture is contacted with the thermolabile DNase under conditions which permit digestion of any double-stranded DNA therein, heating said reaction mixture to inactivate said DNase and thereafter bringing said mixture into contact with target nucleic acid to be amplified.

7. A method as claimed in claim 5 wherein approximately 0.1 units of thermolabile DNase are used per 50 µl of reaction mixture.

8. A method as claimed in claim 5 wherein the nucleic acid sample is present in the reaction mixture before the inactivation of the DNase.

9. The method of claim 5 wherein the nucleic acid contamination is double stranded DNA.

10. A method as claimed in claim 5 wherein the amplification reaction is a polymerase chain reaction (PCR).

11. A kit comprising a thermolabile DNase which is substantially specific for double-stranded DNA, wherein said DNase is derived from the species *Pandalus borealis*, or is a functional equivalent thereof, and optionally nucleotide triphosphates, oligonucleotide primers, a DNA polymerase or DNA ligase and buffers suitable for carrying out nucleic acid amplification reactions.

* * * * *